United States Patent [19]
Burris

[11] Patent Number: 5,213,773
[45] Date of Patent: * May 25, 1993

[54] TREATMENT OF LIQUID ON DEMAND

[76] Inventor: William A. Burris, 7 E. Jefferson Circle, Pittsford, N.Y. 14534

[*] Notice: The portion of the term of this patent subsequent to May 4, 2010 has been disclaimed.

[21] Appl. No.: 848,835

[22] Filed: Mar. 10, 1992

Related U.S. Application Data

[63] Continuation-in-part of Ser. No. 670,690, Mar. 18, 1991, which is a continuation-in-part of Ser. No. 575,622, Aug. 31, 1990, Pat. No. 5,082,558.

[51] Int. Cl.⁵ .............................................. B01D 11/04
[52] U.S. Cl. .................................... 422/256; 210/138; 210/143; 210/188; 422/116; 422/186.07; 422/186.1; 422/305
[58] Field of Search ............... 422/28, 116, 119, 255, 422/305, 292, 256, 186.07, 186.08, 186.1, 907; 210/188, 167, 136, 138, 143, 194

[56] References Cited

U.S. PATENT DOCUMENTS

| | | | |
|---|---|---|---|
| 3,382,980 | 5/1968 | Silva | 210/98 |
| 3,445,001 | 5/1969 | LaRaus | 210/98 |
| 3,699,776 | 10/1972 | LaRaus | 62/157 |
| 3,823,728 | 7/1974 | Burris | 137/88 |
| 4,555,335 | 11/1985 | Burris | 210/192 |
| 4,599,166 | 7/1986 | Gesslauer | 210/961 |
| 4,619,763 | 10/1986 | O'Brien | 210/177 |
| 4,767,525 | 8/1988 | Campbell et al. | 210/87 |
| 4,767,528 | 8/1988 | Sasaki et al. | 210/177 |
| 4,842,723 | 6/1989 | Parks et al. | 210/95 |

Primary Examiner—Robert J. Warden
Assistant Examiner—Krisanne M. Thornton
Attorney, Agent, or Firm—Eugene Stephens & Associates

[57] ABSTRACT

A liquid treatment system receives untreated liquid from a pressurized source and outputs treated liquid on demand. An ozone containing gas from a generator is combined with untreated liquid to accomplish the desired treatment before the liquid is output; and the necessary operations include pumping, venting, a demand event switch, and a control system to accomplish the necessary functions. A valved liquid passageway conducts untreated liquid to a contact region, accumulated gas is vented from the system. A demand event can be manual operation of an output switch or manual operation of an outflow valve that causes a liquid level change within the system. Treated liquid outflow can occur by gravity, as a passive outflow in response to opening an inflow valve, and as an active outflow driven by a pump.

45 Claims, 6 Drawing Sheets

TREATMENT OF LIQUID ON DEMAND

RELATED APPLICATIONS

This application is a continuation-in-part of my copending parent application Ser. No. 670,690, filed 18 Mar. 1991, entitled BATCH LIQUID PURIFIER, which in turn is a continuation-in-part of grandparent application Ser. No. 575,622, filed 31 Aug. 1990, entitled CONTACT LENS PURIFICATION SYSTEM, and issued on 21 Jan. 1992 as U.S. Pat. No. 5,082,558. The full disclosure of parent application Ser. No. 670,690 is hereby incorporated by reference into this application.

TECHNICAL FIELD

This invention involves ozone purification or treatment of liquid with equipment made small enough and inexpensive enough to deal with small quantities of liquid on a demand basis.

BACKGROUND

By this invention, I have reduced the size, complexity, and expense of equipment for treating liquid with ozone on a demand basis; and by carefully selecting and combining components, I have been able to make smaller scale ozone treatment equipment operate conveniently and reliably for safely treating liquid rapidly for small volumes and flow rates. Equipment according to my invention can be operated under a residential countertop, for example, to treat liquid flow on a small scale.

SUMMARY OF THE INVENTION

The liquid treatment system of this invention is connected to a pressurized source of untreated liquid to provide ozone treated liquid on demand by using a generator that makes an ozone containing gas. The treatment system includes a valved passageway and a pumping system arranged for contacting untreated liquid with the ozone containing gas for an interval sufficient to accomplish the intended treatment. A control system responds to a demand event to actuate the generator and the pumping system to make the contact occur between untreated liquid entering the system and ozone containing gas output by the generator. The demand event involves a switch in communication with a control system, and the switch is arranged so that manual action by a user demanding treated liquid changes the state of the switch to initiate a treatment cycle. The manual activity can change the state of the demand switch in two ways—directly by moving the demand switch, and indirectly by opening a treated liquid outflow valve to change a liquid level within the system and thereby change the state of the demand switch. The control system is also arranged to operate during each treatment cycle compatibly with one of several different outflows of treated liquid. These include a gravity outflow in response to opening an output valve from a treated liquid reservoir, a passive outflow in response to opening an inflow valve under control of the control system so that liquid inflow causes outflow of treated liquid, and active outflow in response to actuating a pump controlled by the control system to cause a pumped outflow of treated liquid.

BRIEF DESCRIPTION OF THE DRAWINGS

All of the drawings are partially schematic diagrams of different preferred embodiments of my demand liquid treatment system. Each embodiment includes an ozone generator, a control system, a venting system, a pumping system for bringing ozone into contact with liquid to be treated, and a reducer for diminishing the concentration of any escaping ozone. The different embodiments include different ways of contacting untreated liquid with ozone containing gas; different ways of initiating a demand event, to start a treatment cycle; and different ways of outflowing treated liquid. The various embodiments of the drawings differ from each other in that.

DETAILED DESCRIPTION

Figure 1:
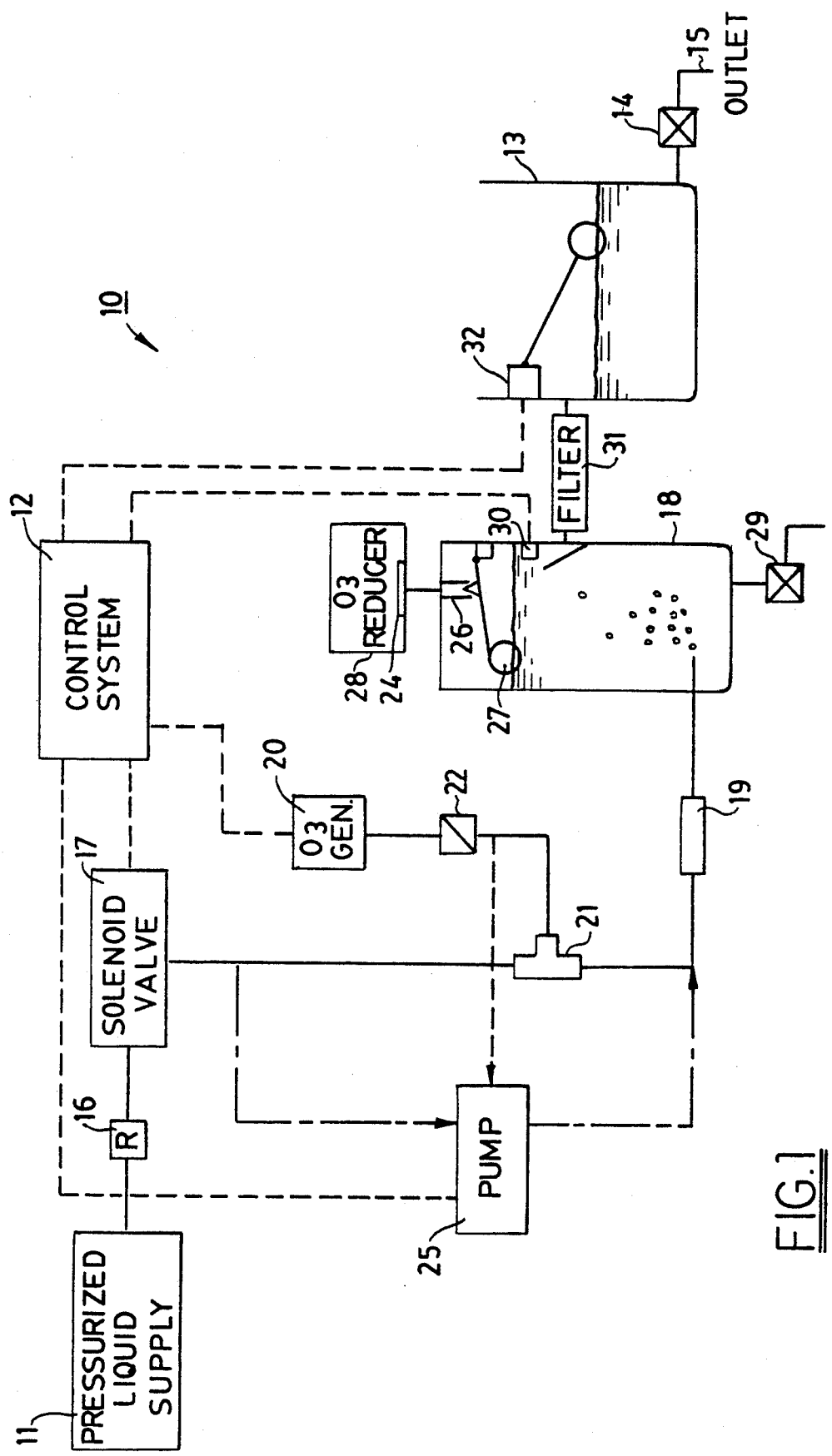
FIGS. 1 and 2 show a contacting chamber upstream of a treated liquid reservoir, and different ways of bringing about contact between untreated liquid and ozone containing gas.

The preferred embodiments of the drawings have comparative advantages in features such as convenience, reliability, safety, cost, and compactness. Different embodiments, using different combinations of such features, may be preferred for different users with different desires. The embodiments will be explained in the order presented in the drawings, but this does not imply any similar order of importance. Also, some of the different features that are illustrated in the drawings can be interchanged among the various embodiments; and the drawings are arranged to illustrate the different features that can be combined, and not to delimit one combination of features from another.

The reasons that the preferred embodiments can be varied so extensively include the many different uses for liquid treatment and the correspondingly different considerations for expense, space requirements, and demand size. Different users will require different levels of sophistication in convenience and extent of automatic performance.

One important use is treating water for drinking and cooking purposes. This can be done to supply a countertop or sink having an outlet for treated or purified water. Water can also be treated on a demand basis for small scale requirements in laboratories, offices, and industries, where the treated liquid can be used for many different purposes. The liquid to be treated is not necessarily water; and my treatment can be applied to treating saline solution, for example. This could be desirable in an optometrist's office, for cleaning, rinsing, disinfecting, and storing contact lenses. Disinfected liquids, or liquids treated to contain dissolved ozone, as provided by my system can also be used for an unlimited variety of purposes such as rinses, washes, or storage for dental, medical, or any other purposes.

The liquid treatment system 10 of FIG. 1 treats raw liquid from a pressurized liquid supply 11 in response to a demand event, as explained below. A control system 12 operates treatment system 10 to contact untreated liquid with an ozone containing gas and to deliver treated liquid to an outlet 15. Treated liquid is stored in a reservoir 13 upstream of outlet 15, which outputs treated liquid on demand by the opening of valve 14.

A pressure or flow reducing or regulating valve 16 regulates the pressure of untreated liquid entering system 10 via a solenoid valve 17 operated by control system 12. When solenoid valve 17 is opened, untreated liquid flows into contact chamber 18 where an ozone containing gas output by generator 20 contacts and treats the liquid. Initial contact of the liquid and gas occurs upstream of chamber 18 in either of two ways, as shown in FIG. 1. Inflow of untreated liquid through a venturi 21 can draw ozone containing gas from generator 20 via check valve 22 into contact with inflowing liquid so that the liquid and gas are mixed together, and their combined flow is delivered to contact chamber 18, possibly via an inline mixer 19. An alternative, shown in broken lines in FIG. 1, uses a pump 25 in place of venturi 21. Pump 25 has inputs for both untreated liquid from solenoid valve 17 and ozone containing gas from check valve 22, and pump 25 combines and mixes these and delivers them to chamber 18. Pump 25, like solenoid valve 17 and generator 20, is operated by control system 12.

Treatment chamber 18 operates under a pressure established by regulator valve 16, which is preferably moderately above atmospheric pressure. A vent 26 at the top of treatment chamber 18 is operated by a float valve 27 so that when gas accumulates at the top of chamber 18, forcing the liquid level downward, vent 26 opens to vent gas to atmosphere. An ozone reducer 28 reduces the concentration of any ozone escaping to atmosphere. Chamber 18 also has a valved drain 29 and preferably includes a sensor 30 in communication with control system 12 for determining that treatment of liquid in chamber 18 is adequate. This can be done by detecting the concentration of dissolved ozone in liquid within chamber 18.

Outflow from treatment chamber 18 preferably occurs via filter 31 to treated liquid reservoir 13, the liquid level of which is monitored by float switch 32. When treated liquid is withdrawn from outlet 15, by manually operated valve 14, the liquid level in reservoir 13 drops, actuating switch 32 which communicates with control system 12. This serves as a demand event in response to which control system 12 initiates a treatment cycle by operating generator 20, solenoid valve 17, and possibly pump 25 so that untreated liquid flows into system 10 and becomes contacted with ozone containing gas.

Besides conventional check valving, check valve 22 can be formed of porous hydrophobic material that allows gas to pass through but prevents any liquid backflow from reaching generator 20. This is especially desirable when generator 20 is the preferred corona discharge generator that would be damaged by presence of any liquid. Suitable porous hydrophobic materials can include hydrophobic resin or plastic materials that are made porous to allow passage of gas but block the passage of liquid. Porous inorganic materials may also be usable for this. The entire material does not need to be hydrophobic so long as hydrophobic material is arranged to serve as a liquid barrier combined with an otherwise porous material. These considerations also apply to other uses of porous hydrophobic materials in my systems, as mentioned below.

Although ambient air is a simple and preferred input for generator 20, it is also possible to use dried air that has passed through a dryer to help keep moisture out of generator 20. Another possibility is supplying oxygen from a small container serving as the input to generator 20, which can produce more ozone from an oxygen supply than from an air supply.

Ozone reducer 28 contains at least one of several materials that are available for reducing the ozone concentration or changing the ozone into ordinary oxygen so that raw ozone does not escape into the atmosphere. Even if raw ozone were to escape through vent 26, however, it should not present any health hazard in the small quantities used for operating system 10.

There are several ways that gas and liquid can be separated after treatment. In system 10, the liquid level in chamber 18 is preferably controlled by a float valve 27, which vents excess gas while keeping the liquid pressurized. Gravity can also be used to provide a liquid surface above which gas can rise. Another possibility is to arrange a porous hydrophobic element to form a barrier for liquid, while allowing gas to pass. The liquid and gas separation can occur separate from a liquid reservoir or purified liquid storage, or can be combined with these, as shown in other embodiments.

When reducer 28 is used and is filled with a catalytic or reactive material that reduces the ozone concentration or changes the ozone into oxygen, it is important that liquid not reach the material within reducer 28, because liquid would impair its action. Working against this is the fact that gas bubbles can enter and burst within reducer 28, creating spray droplets. Baffles are one possibility for keeping these spray droplets out of reducer 28, but baffles would not block liquid flow if the system were overturned. What I prefer, therefore, is a porous hydrophobic element 24 that allows gas, but not liquid, to enter reducer 28.

Sensor 30 can be arranged elsewhere within my system so long as it is wetted with liquid that is subject to treatment by contact with an ozone containing gas. Control system 12 preferably includes a timer that times the operation of a treatment cycle in response to the concentration of dissolved ozone detected by sensor 30.

Filter 31 can contain activated carbon or a catalyst that greatly reduces the concentration of dissolved ozone remaining in the purified liquid. This can be advantageous in situations requiring that little or no dissolved ozone remain in the treated liquid that is output from chamber 18. Other ways of ensuring this are to let the treated liquid stand for a few minutes before using it, to aerate the treated liquid before using it, or to subject the treated liquid to ultraviolet light. For most purposes, dissolved ozone is acceptable in the purified liquid; and no health hazard has yet been identified with directly consuming water containing dissolved ozone at levels found in system 10. For some purposes, such as rinsing or disinfecting, dissolved ozone in the treated liquid output may be desirable.

Figure 2:
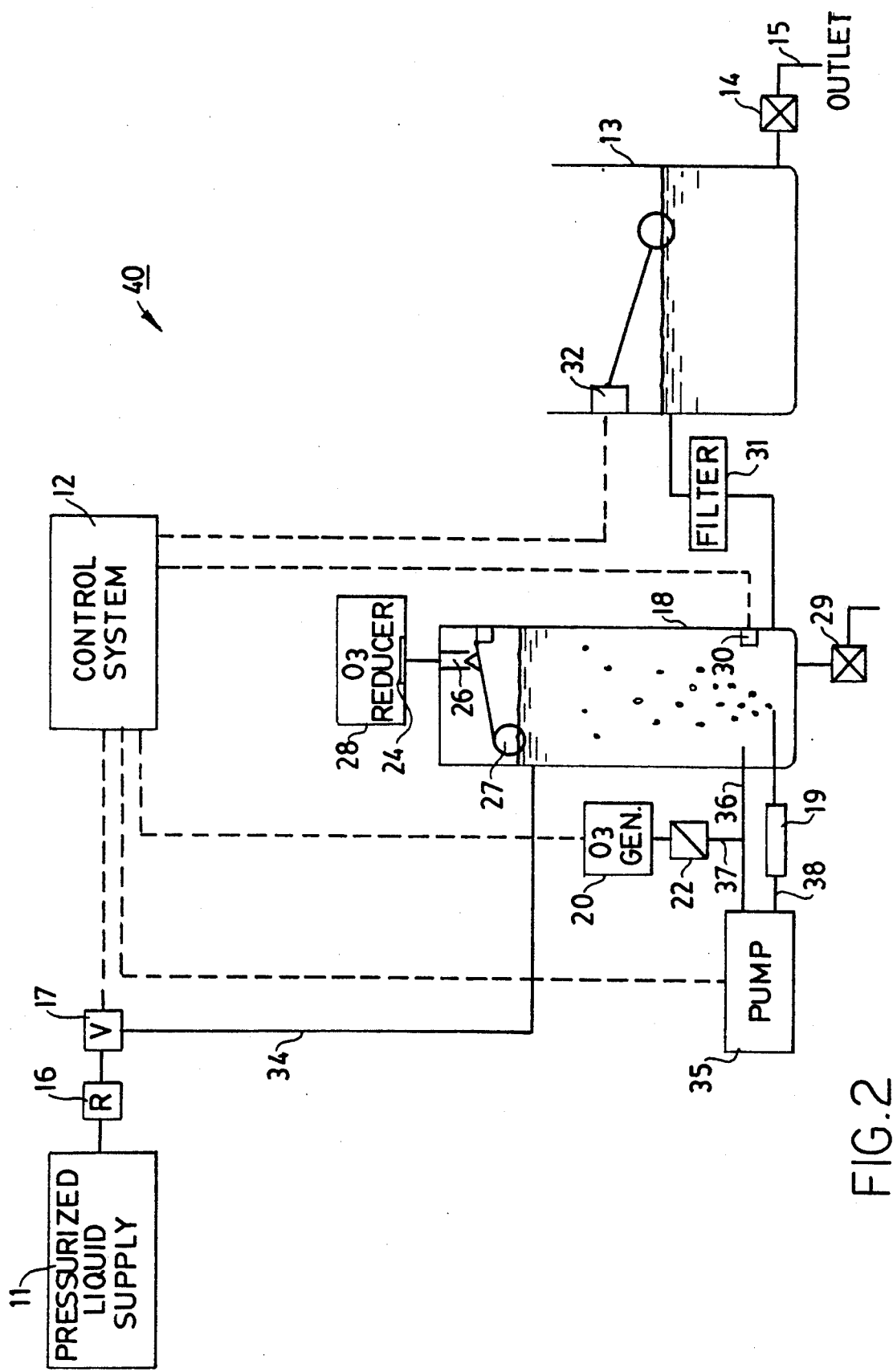

The treatment system 40 of FIG. 2 is similar to system 10 of FIG. 1 and includes many similar components. The principal difference is the way pump 35 is arranged for contacting liquid to be treated with an ozone containing gas from generator 20. Pump 35, which is preferably a positive displacement pump, draws liquid from treatment chamber 18 through line 36, which is connected with output line 37 from generator 20 downstream of check valve 22. This draws both liquid and ozone containing gas into pump 35, where the liquid and gas are mixed together and are discharged via line 38, which can include inline mixer 19. This circulates liquid from treatment chamber 18 through pump 35 and directs dissolved and gaseous ozone into chamber 18, for treatment purposes.

Untreated liquid from source 11 enters chamber 18 via line 34 from solenoid valve 17, downstream of pressure regulator or flow control device 16. Untreated liquid entering an upper region of treatment chamber 18 and an ozone and liquid mixture entering a lower region of chamber 18 establish a countercurrent gas/liquid flow that facilitates contacting the liquid with ozone.

Otherwise, system 40 and its possible alternatives are similar to those explained above for system 10. A demand event, initiating a treatment cycle, occurs when outlet valve 14 is opened to draw off treated liquid from reservoir 13 to an extent that actuates control system 12. This initiates a treatment cycle and admits untreated liquid from source 11 into treatment chamber 18, which is vented as previously explained.

Figure 3:
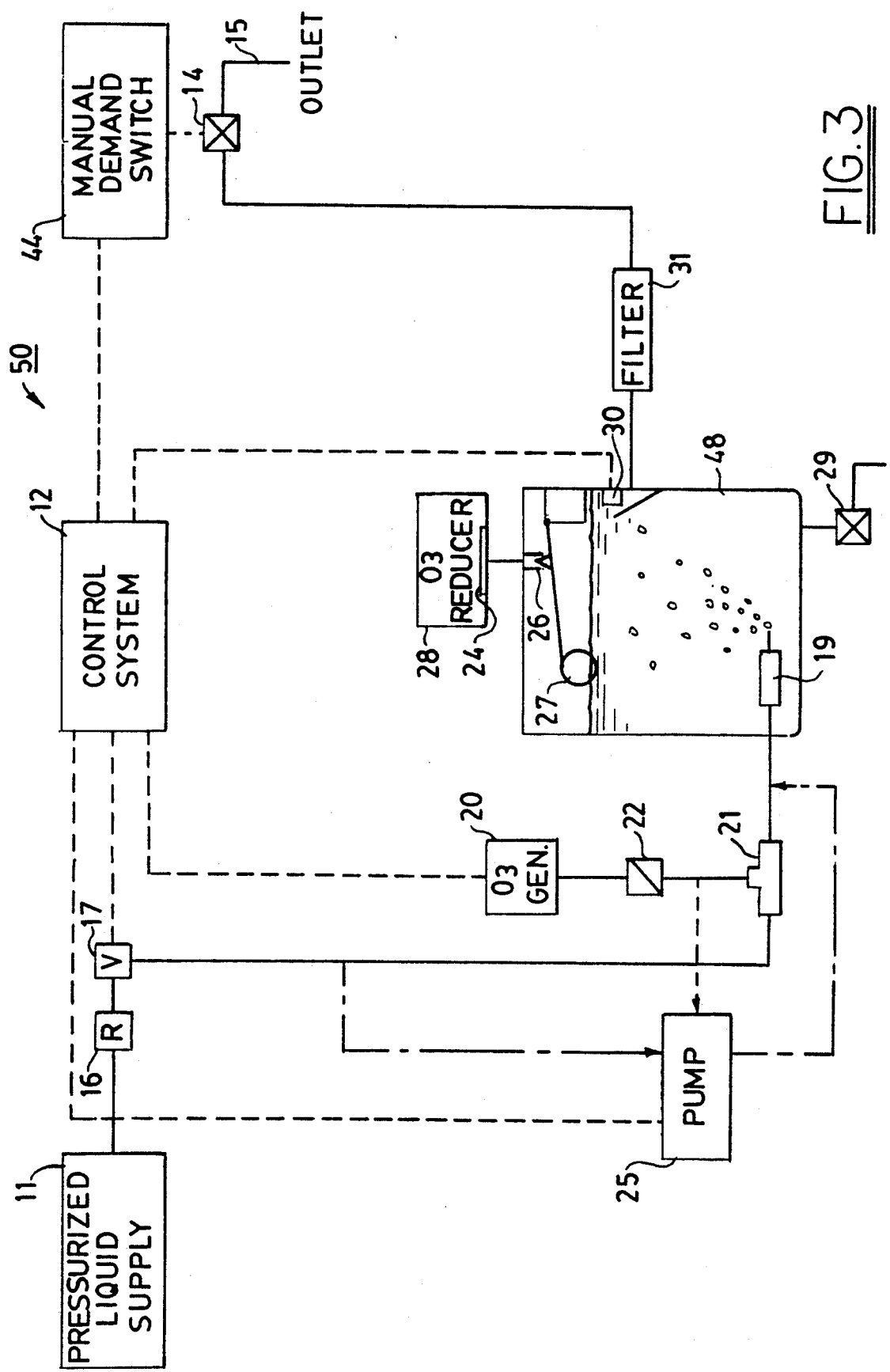
FIGS. 3 and 4 show output of treated liquid from a contact or treatment chamber supplied in various ways with untreated liquid and ozone containing gas.

System 50 of FIG. 3 is also similar in many respects to system 10 of FIG. 1. It differs primarily in the way that treated liquid is output and the way that an output demand event initiates a treatment cycle.

Output of treated liquid from system 50 is directly from treatment chamber 48, which is otherwise similar to treatment chamber 18 of system 10. Chamber 48 has a vent 26 controlled by a float valve 27 to vent accumulated gas to atmosphere via ozone reducer 28, which can be protected by a porous hydrophobic element 24, as explained above. The input of untreated liquid and ozone containing gas into chamber 48 can be the same as described for system 10, and pressure or flow regulating device 16 establishes a moderate liquid pressure within chamber 48, sufficient to cause an outflow of treated liquid on demand.

Outflow from treatment chamber 48 is preferably via filter 31 and preferably under manual control, as represented by manual demand switch 44. There are several ways that manual demand switch 44 can be arranged for operation. One way is an electric switch communicating with control system 12, which opens inlet valve 17, causing liquid flow into and through the system and outflow of treated liquid through outlet 15. Another possibility is a valve 14 opening outlet 15 in a way that controls system liquid flow, either alone or in combination with inlet valve 17. Switch 44 can operate valve 14 electrically, while communicating with control system 12, and a manually operated valve 14 can actuate switch 44 to signal control system 12 to initiate a treatment cycle when valve 14 is opened. These alternatives can also be combined in various ways in this and in other embodiments. When a demand event occurs, however initiated, additional untreated liquid is admitted to treatment chamber 48 while control system 12 operates ozone generator 20 to direct an ozone containing gas to chamber 48, either via venturi 21 or via pump 25, and possibly via mixer 19, as previously explained for system 10.

Figure 4:
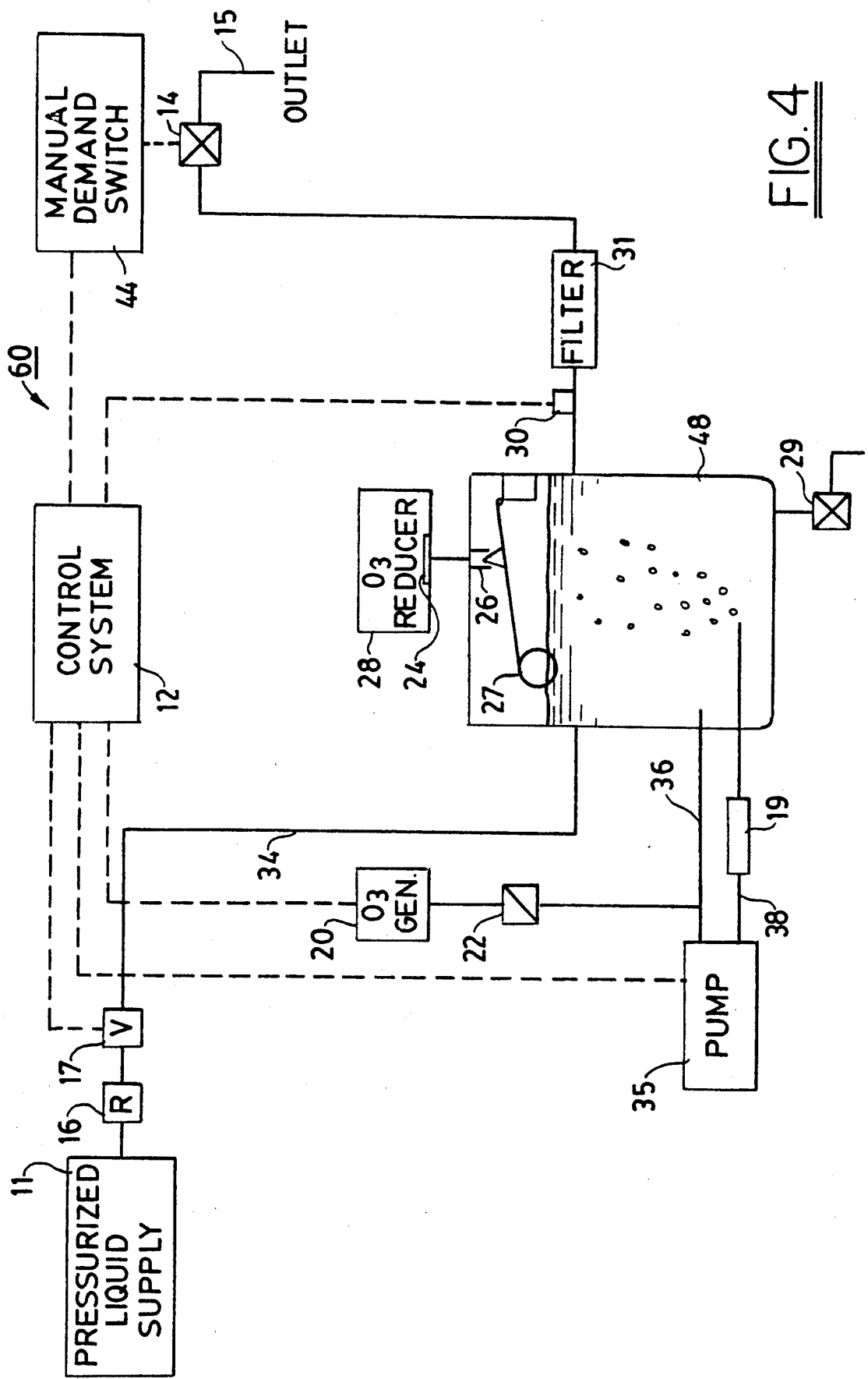

System 60 of FIG. 4 is similar to system 50 of FIG. 3, in using treatment chamber 48 and treated liquid output via manual demand switch 44. System 60 is otherwise similar to system 40 of FIG. 2 in the way untreated liquid and an ozone containing gas are directed into treatment chamber 48 via pump 35 and lines 36 and 38, as explained above. Except for the inflow to treatment chamber 48, which is similar to that of system 40, and for the different position of ozone sensor 30, the operation of system 60 is similar to the operation of system 50.

Figure 5:
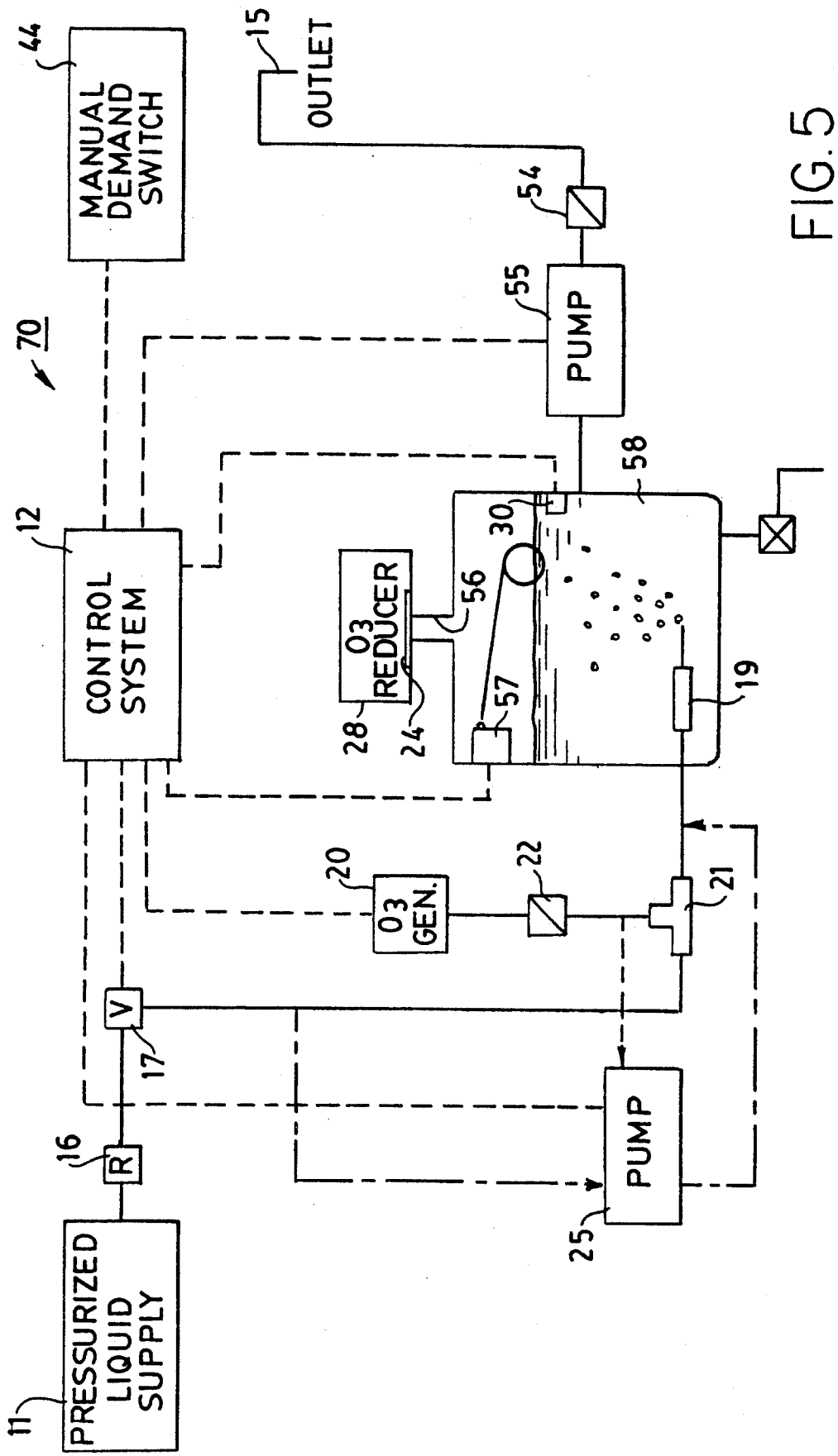
FIGS. 5 and 6 show an unpressurized liquid treatment chamber supplied in different ways with untreated liquid and ozone containing gas so that treated liquid can be pumped out of the contact chamber to a system output.

System 70 of FIG. 5 uses a substantially unpressurized treatment chamber 58 where an ozone containing gas is contacted with liquid to be treated. Liquid level in chamber 58 is sensed by a switch 57 that communicates with control system 12. When liquid level drops sufficiently in chamber 58, switch 57 communicates this to control system 12, which initiates a treatment cycle directing additional untreated liquid into chamber 58, along with an ozone containing gas, for treating the liquid. The ways that the untreated liquid and ozone containing gas can be introduced into chamber 58 are the same as in systems 10 and 50, as explained above.

The venting of accumulated gas from treatment chamber 58 is not controlled by a vent valve, as in systems 10, 40, 50, and 60, but occurs continuously, whenever gas pressure exceeds atmospheric pressure. Although vent 56 is not float valve controlled, it is similar to previously described venting systems in that it leads to atmosphere via ozone reducer 28, which is preferably protected by a porous hydrophobic element 24.

The output of treated liquid from chamber 58 is provided by pump 55, which is operated by control system 12 in response to operation of manual demand switch 44 at outlet 15. A check valve 54 prevents treated liquid from flowing back toward pump 55 from the direction of outlet 15. Actuation of demand switch 44 thus turns on pump 55, to cause treated liquid to flow out of outlet 15. As this occurs, liquid level in treatment chamber 58 falls; and if enough liquid is withdrawn to actuate liquid level switch 57, this initiates a treatment cycle, replenishing the liquid and the ozone containing gas to treatment chamber 58.

Operating treatment chamber 58 in an unpressurized or substantially atmospheric state and using pump 55 to supply a treated liquid output has several advantages. Chamber 58 can be inexpensive and can be located below the level of outlet 15. Pump 55 can flow treated liquid upward a level or two above treatment chamber 58, to the location of outlet 15. Keeping the pressure low in chamber 58 also facilitates the introduction of an ozone containing gas by reducing the output pressure that must be overcome by ozone generator 20. It can also ensure an adequate pressure drop between regulator valve 16 and chamber 58 so that venturi 21 works satisfactorily as a means of combining untreated liquid with an ozone containing gas directed to chamber 58. Of course, pump 25 can serve as a viable alternative to venturi 21, as previously explained.

Figure 6:
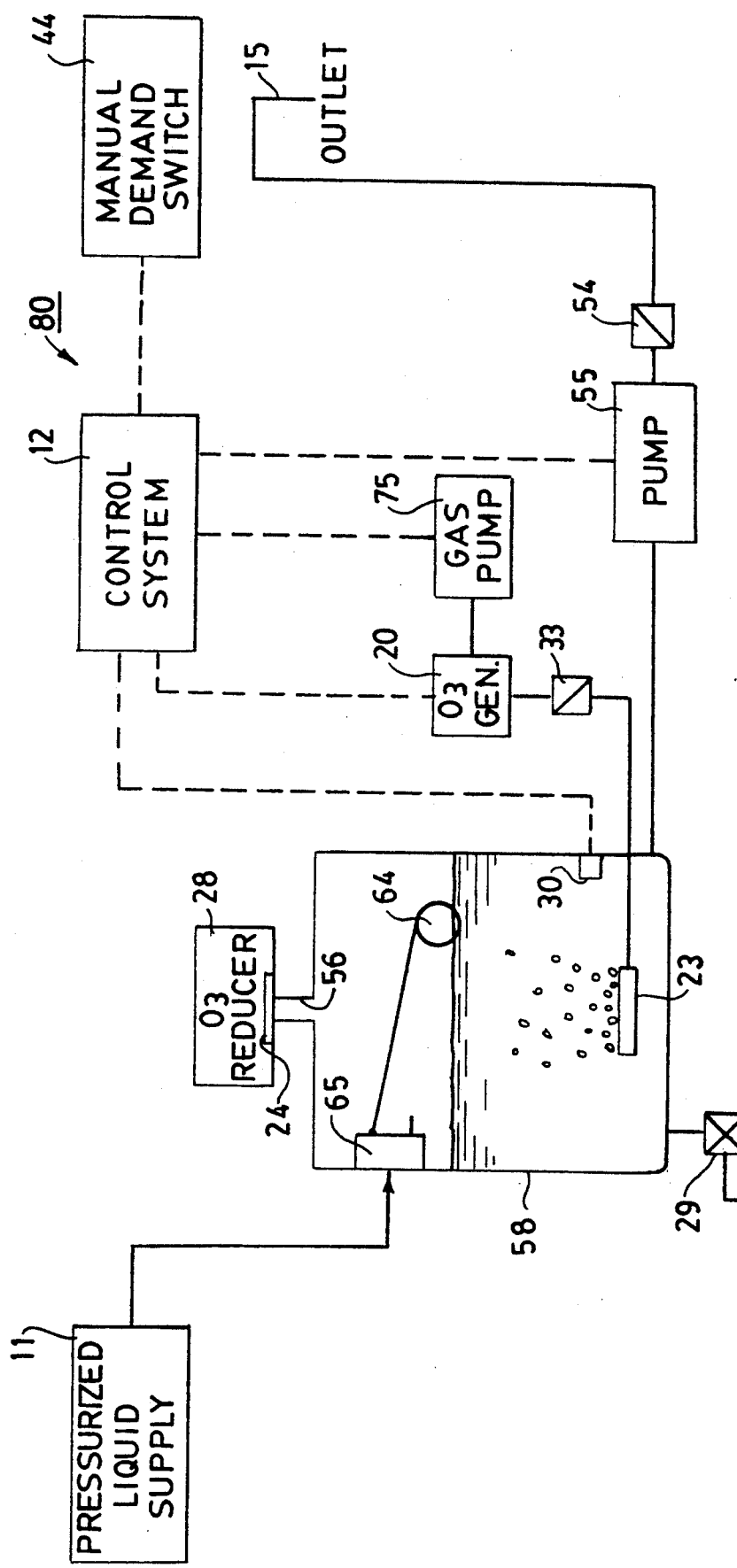

System 80 of FIG. 6 is similar to system 70 of FIG. 5 in using a low cost, unpressurized treatment chamber 58 vented to atmosphere via vent 56, ozone reducer 28, and protective element 24. Also, output of treated liquid via pump 55, check valve 54, and manual demand switch 44 near outlet 15 is as explained above relative to system 70. System 80 differs primarily in the way liquid and ozone containing gas are introduced into treatment chamber 15, under operation of control system 12.

A float valve 65 connected to pressurized liquid supply 11 and having a float element 64 controls the inflow of untreated liquid into chamber 58. When the level of liquid falls in chamber 58, float element 64 lowers and opens valve 65 to admit additional liquid from pressurized source 11, to keep chamber 58 replenished. This can occur without any intervention being required from control system 12 so that chamber 58 and the means for keeping it filled with liquid are both inexpensive.

Whenever treated liquid output occurs by operation of manual demand switch 44, to turn on pump 55, this also causes control system 12 to initiate a treatment cycle, which preferably occurs whether or not valve 65 admits untreated liquid to chamber 58. Often, an outflow through outlet 15 will be adequate to open valve 65, to admit untreated liquid to chamber 58; but whether or not this occurs, a treatment cycle is preferably initiated by the demand event to ensure that liquid in chamber 58 is properly treated. For each treatment cycle, gas pump 75 actuates to supply air or oxygen to ozone generator 20, which outputs an ozone containing gas to sparge element 23, via check valve 33. This bubbles a sufficient amount of ozone containing gas into the liquid in treatment chamber 58 to accomplish the desired treatment of the liquid. This can be detected by sensor 30, which communicates with control system 12 to determine the amount of dissolved ozone in liquid in chamber 58.

Chamber 58 thus stores treated liquid ready for output any time that manual demand switch 44 is operated. Using pump 55 for treated liquid outflow, besides being simple and inexpensive, offers the advantage of delivering treated liquid to a point substantially above the level of treatment chamber 58.

I claim:

1. A liquid treatment system connected to a pressurized source of untreated liquid to provide treated liquid on demand, said system using a generator that makes an ozone containing gas and comprising a pressurized source of untreated liquid and a generator that makes an ozone containing gas, said system further comprising:
   a. a valved liquid passageway for conducting said liquid from said source through said system to an outflow via a contact region;
   b. a pumping system for causing said ozone containing gas to flow from said generator into said contact region; said pumping system and said passageway leading to said contact region being sized to determine the flow rates of said ozone containing gas and said liquid into said contact region
   c. a containment system arranged for containing said liquid downstream of said contact region at a liquid pressure lower than the pressure of said source;
   d. a control system arranged for operating said generator, said pumping system, and said valved liquid passageway during each treatment cycle to deliver said untreated liquid and said ozone containing gas to said contact region and to deliver treated liquid to an output from said liquid treatment system; said control system being operable automatically to initiate said treatment cycle in response to a demand event indicating a demand for treated liquid; said control system being arranged to operate during each treatment cycle compatibly with a predetermined one of a plurality of said outflows of treated liquid from said treatment system, said outflows including gravity outflow in response to opening said output valve from said treated liquid reservoir, passive outflow in response to opening an inflow valve under control of said control system so that liquid inflow causes outflow of said treated liquid, and active outflow in response to actuating a pump controlled by said control system to cause outflow of said treated liquid
   e. a demand switch arranged in communication with said control system to provide said demand event by changing state in response to a manually activated system operable in a predetermined one of a pair of direct and indirect configurations, said direct configuration comprising arrangement of said manually activated system for directly operating said demand switch, and said indirect configuration comprising arrangement of said manually activated system for operating an output valve for drawing treated liquid from a treated liquid reservoir, the liquid level of which controls the state of said demand switch.

2. The liquid treatment system of claim 1 including a liquid filter arranged downstream from said source.

3. The liquid treatment system of claim 1 including a gas venting system arranged for enabling gas to escape from said system after said contact while preventing liquid from escaping from said system.

4. The liquid treatment system of claim 3 wherein said venting system includes a porous hydrophobic material arranged to allow gaseous outflow while blocking liquid outflow.

5. The liquid treatment system of claim 3 wherein said venting system is arranged for reducing the escape of ozone to the atmosphere.

6. The liquid treatment system of claim 1 including a porous hydrophobic material arranged for preventing liquid from contacting an ozone escape reducing element in said venting system.

7. The liquid treatment system of claim 1 including means for preventing flow of liquid into said generator.

8. The liquid treatment system of claim 7 wherein said flow preventing means includes a porous hydrophobic material arranged for blocking liquid flow and for allowing flow of said ozone containing gas.

9. The liquid treatment system of claim 1 wherein said pumping system includes a venturi arranged so that when said liquid passes through said venturi, said ozone containing gas is drawn from said generator into said venturi.

10. The liquid treatment system of claim 1 wherein said pumping system includes a pump arranged for pumping and mixing said liquid and said ozone containing gas.

11. The liquid treatment system of claim 1 wherein said pumping system includes a gas pump for pumping said ozone containing gas from said generator to said contact region.

12. The liquid treatment system of claim 1 wherein said treated liquid reservoir is at atmospheric pressure.

13. The liquid treatment system of claim 1 wherein said control system is arranged for operating said generator and said pumping system for at least a minimum time during each treatment cycle to ensure sufficient treatment.

14. The liquid treatment system of claim 1 including a sensor arranged for sensing the concentration of ozone in said liquid and wherein said control system is arranged to be responsive to said sensor for treating said liquid.

15. A demand type of liquid treatment system receiving untreated liquid from a pressurized source and outputting treated liquid on demand, said system using a generator that provides an ozone containing gas, and said system comprising a pressurized liquid source and a generator that provides an ozone containing gas, said system further comprising:
   a. a manually operable output switch arranged to cause outflow of treated liquid from said system;

b. a valved passageway for controlling flow of liquid from said pressurized source to an outflow through a reduced pressure region within said treatment system;

c. a control system arranged responsively to said output switch for initiating a treatment cycle of said system; said control system causing said generator to operate during said treatment cycle; said control system being arranged for opening said valved passageway to admit untreated liquid to said treatment system upon initiation of said treatment cycle, said control system being arranged to further operate compatibly with a predetermined one of a plurality of outflows of said treated liquid from said system, said outflows including gravity outflow in response to opening an output valve activated by said manually operable switch, passive outflow in response to opening said valved passageway by said control system in response to said manually operable switch so that liquid inflow causes outflow of said treated liquid, and active outflow in response to a pump operated by said control system in response to said manually operable switch for causing outflow of said treated liquid from said system;

d. a pumping system arranged for causing said ozone containing gas to flow from said generator to a region where ozone containing gas contacts liquid in said system;

said pumping system being actuated by said control system upon initiation of said treatment cycle.

16. The system of claim 15 including a contacting chamber and means for bubbling said ozone containing gas into contact with a quantity of said liquid in said contact chamber.

17. The system of claim 16 including means for separating said ozone containing gas from said liquid after contact.

18. The system of claim 15 including a gas venting system arranged for enabling gas to escape from said system after said contact while preventing liquid from escaping from said system.

19. The system of claim 18 wherein said venting system includes an element arranged for reducing the escape of ozone to the atmosphere.

20. The system of claim 18 including a porous hydrophobic material arranged for preventing liquid from contacting said ozone escape reducing element.

21. The system of claim 15 wherein said pumping system includes a venturi arranged so that when said liquid passes through said venturi, said ozone containing gas is drawn from said generator into said venturi.

22. The system of claim 15 wherein said pumping system includes a pump arranged for pumping and mixing said liquid and said ozone containing gas.

23. The system of claim 15 wherein said pumping system includes a gas pump for pumping said ozone containing gas from said generator to said contact region.

24. The system of claim 15 including a filter arranged upstream of said output.

25. The system of claim 15 including a reservoir of treated liquid and a liquid level sensing switch arranged in said reservoir in communication with said control system.

26. The system of claim 15 wherein said reduced pressure region includes a treated liquid reservoir arranged so that said outflows occur from said reservoir.

27. The system of claim 15 including means for preventing flow of liquid into said generator.

28. The system of claim 27 wherein said flow preventing means includes a porous hydrophobic material arranged for blocking liquid flow and for allowing flow of said ozone containing gas.

29. The system of claim 15 wherein said control system is arranged for operating said generator and said pumping system for at least a minimum time interval after initiating a treatment cycle.

30. The system of claim 15 including a sensor arranged for sensing the concentration of ozone in said liquid, and said control system is arranged to be responsive to said sensor for treating said liquid.

31. A liquid treatment system receiving untreated liquid from a pressurized source and providing a treated liquid on demand, said system using a generator that provides an ozone containing gas, and said system comprising: a pressurized source of untreated liquid and a generator that provides ozone containing gas, said system further comprising a. an unpressurized containment chamber arranged upstream of an output from said treatment system;

b. a pumping system arranged for flowing said ozone containing gas from said generator to a region where said ozone containing gas contacts untreated liquid;

c. a demand switch arranged to provide a demand event by changing state in response to a manually activated system operable in a predetermined one of a pair of direct and indirect configurations, said direct configuration comprising arrangement of said manually activated system for directly operating said demand switch, and said indirect configuration comprising arrangement of said manually activated system for operating a valve for drawing treated liquid from said containment chamber, the liquid level of which controls the state of said demand switch;

d. a control system arranged responsively to change of state of said demand switch for initiating a treatment cycle during which said generator and said pumping system are operated for controlling flow of said liquid and said ozone containing gas through said treatment system; and said control system being arranged to operate during each treatment cycle compatibly with a predetermined one of a plurality of outflow arrangements for outflowing treated liquid from said treatment system, said outflow arrangements including gravity outflow in response to opening an output valve from said containment chamber, passive outflow in response to opening an inflow valve under control of said control system so that liquid inflow causes outflow of said treated liquid, and pumped outflow in response to actuating a pump controlled by said control system to cause outflow of said treated liquid from said containment chamber.

32. The system of claim 31 including a filter arranged upstream of said outflow arrangements.

33. The system of claim 31 including means for separating said ozone containing gas from said liquid after contact.

34. The system of claim 31 including a gas venting system arranged for enabling gas to escape from said system after said contact while preventing liquid from escaping from said system.

35. The system of claim 34 wherein said venting system includes an element arranged for reducing the escape of ozone to the atmosphere.

36. The system of claim 34 including a porous hydrophobic material arranged for preventing liquid from contacting said ozone escape reducing element.

37. The system of claim 31 wherein a valved passageway controlled by said control system is arranged for admitting said untreated liquid from said source to said treatment system during said treatment cycle.

38. The system of claim 31 including a float valve arranged for admitting untreated liquid to said containment chamber.

39. The system of claim 31 including means for preventing flow of liquid into said generator.

40. The system of claim 39 wherein said flow preventing means includes a porous hydrophobic material arranged for blocking liquid flow and for allowing flow of said ozone containing gas.

41. The system of claim 31 wherein said control system is arranged for operating said generator and said pumping system for at least a minimum time interval after initiating a treatment cycle.

42. The system of claim 31 including a sensor arranged for sensing the concentration of ozone in said liquid and wherein said control system is arranged to be responsive to said sensor for treating said liquid.

43. The system of claim 31 wherein said pumping system includes a venturi arranged so that when said liquid passes through said venturi, said ozone containing gas is drawn from said generator into said venturi.

44. The system of claim 31 wherein said pumping system includes a pump arranged for pumping and mixing said liquid and said ozone containing gas.

45. The system of claim 31 wherein said pumping system includes a gas pump for pumping said ozone containing gas from said generator to said contact region.

* * * * *